Figure 1:
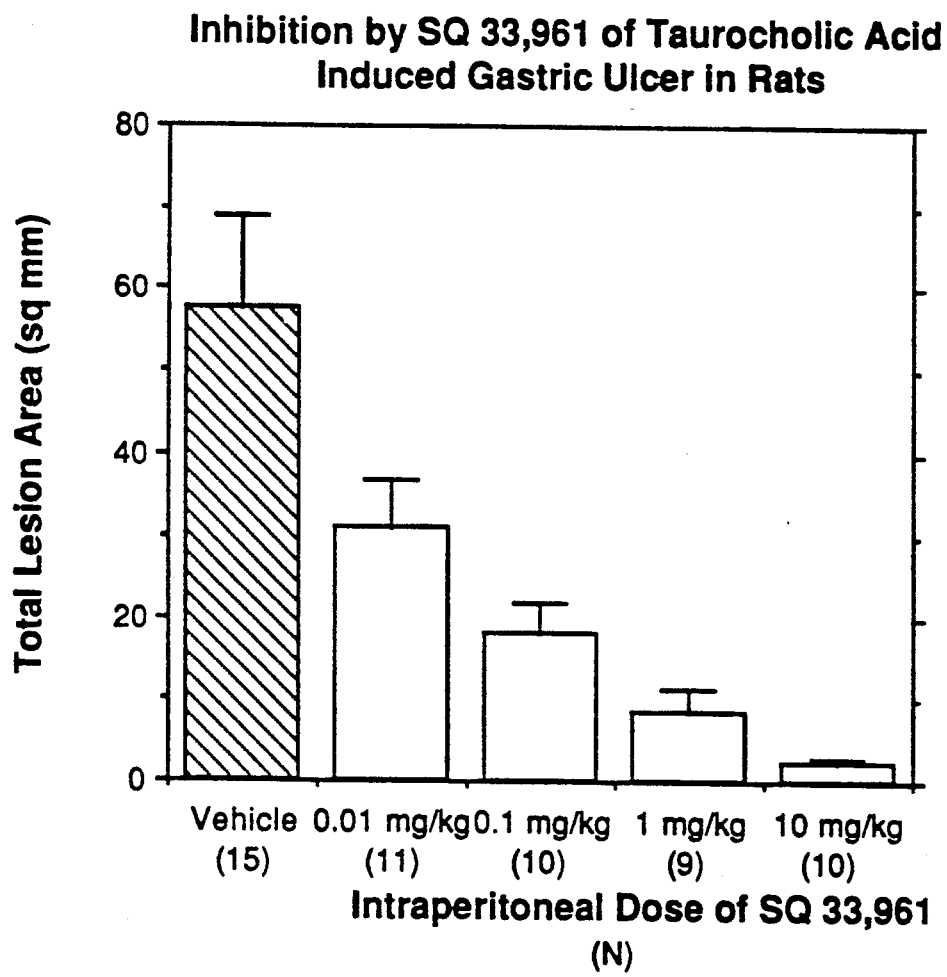

United States Patent [19]
Rubin et al.

[11] Patent Number: 5,312,818
[45] Date of Patent: May 17, 1994

[54] METHOD OF PROTECTING AGAINST AND/OR TREATING ULCERATIVE GASTROINTESTINAL CONDITIONS USING A THROMBOXANE A₂ RECEPTOR ANTAGONIST AND COMBINATION USEFUL IN PREVENTING AND/OR TREATING ULCERS AND/OR INFLAMMATION

[75] Inventors: Bernard Rubin, Lawrenceville, N.J.; Martin L. Ogletree; Eugene H. O'Keefe, both of Newtown, Pa.; A. K. Gunnar Aberg, Lawrenceville, N.J.

[73] Assignee: E. R. Squibb & Sons, Inc., Princeton, N.J.

[21] Appl. No.: 993,876

[22] Filed: Dec. 23, 1992

Related U.S. Application Data

[63] Continuation of Ser. No. 495,865, Mar. 19, 1990, abandoned.

[51] Int. Cl.⁵ .............. A61K 31/55; A61K 31/445; A61K 31/425; A61K 31/42
[52] U.S. Cl. .................... 514/212; 514/326; 514/365; 514/374; 514/381; 514/422; 514/459; 514/925
[58] Field of Search ............. 514/381, 374, 365, 459, 514/212, 326, 422, 925

[56] References Cited

U.S. PATENT DOCUMENTS 4,182,854  4/1986  Hall et al. ............................ 514/469

OTHER PUBLICATIONS

Mochizuki et al. Scand. J. Gastroenterol., 24(Supp. 162), 194–7 (1989).
Gervasi et al, Int. J. Tiss. Reac., V(3), 253–56 (1983).

*Primary Examiner*—Frederick E. Waddell
*Assistant Examiner*—Gregory Hook
*Attorney, Agent, or Firm*—Burton Rodney

[57] ABSTRACT

A method is provided for protecting against and/or treating ulcerative gastrointestinal conditions, including anti-inflammatory drug-induced gastrointestinal ulcers, using a thromboxane A₂ receptor antagonist. In addition, a combination is provided which includes a thromboxane A₂ receptor antagonist and an anti-inflammatory agent which combination may be used to treat inflammatory conditions, such as arthritis, while inhibiting formation of and/or treating gastrointestinal ulcers.

10 Claims, 2 Drawing Sheets

METHOD OF PROTECTING AGAINST AND/OR TREATING ULCERATIVE GASTROINTESTINAL CONDITIONS USING A THROMBOXANE $A_2$ RECEPTOR ANTAGONIST AND COMBINATION USEFUL IN PREVENTING AND/OR TREATING ULCERS AND/OR INFLAMMATION

This is a continuation of application Ser. No. 495,865, filed Mar. 19, 1990, now abandoned.

FIELD OF THE INVENTION

The present invention relates to a method for protecting against and/or treating ulcerative gastrointestinal conditions, including anti-inflammatory-drug-induced ulcers, employing a thromboxane $A_2$ receptor antagonist, to a method for treating inflammatory conditions employing a combination of a thromboxane $A_2$ receptor antagonist and an anti-inflammatory drug while inhibiting formation of and/or treating gastrointestinal ulcers, and to a combination of thromboxane $A_2$ receptor antagonist and anti-inflammatory drug useful in such method.

BACKGROUND OF THE INVENTION

Anti-inflammatory drugs, such as aspirin, indomethacin, ibuprofen, meclofenamate, naproxen, phenylbutazone, piroxicam and various corticosteroids are effective in treating or controlling pain, including headache, and in decreasing joint swelling, tenderness, pain and stiffness in conditions such as rheumatoid arthritis. Unfortunately, although such anti-inflammatory drugs are effective in treating pain and inflammatory conditions, they cause development of gastrointestinal ulcers thereby seriously limiting chronic use of these drugs.

It has now been found that when an anti-inflammatory drug is used in combination with a thromboxane $A_2$ receptor antagonist, the anti-inflammatory drug is still effective in treating inflammation, while the thromboxane $A_2$ receptor antagonist is effective in inhibiting and/or treating gastric erosion and/or gastrointestinal ulcers which may result from treatment with the anti-inflammatory drug. Thus, in effect, thromboxane $A_2$ receptor antagonists are useful for the prevention and treatment of gastric and intestinal lesions in response to anti-inflammatory drugs.

U.S. Pat. No. 4,582,854 to Hall et al, discloses 7-oxabicycloheptane substituted oxa prostaglandin analogs having the structure

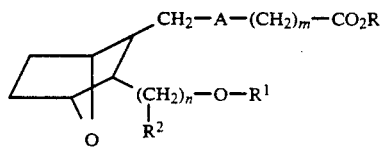

wherein R is hydrogen, lower alkyl, alkali metal or trihydroxymethylaminomethane, $R^1$ is lower alkyl, aryl, aralkyl, cycloalkyl or cycloalkylalkyl, $R^2$ is hydrogen or lower alkyl, A is $-CH=CH-$ or $-(CH_2)_2-$, n is 1 to 4, and m is 1 to 8.

The Hall et al compounds are disclosed as being selective thromboxane $A_2$ receptor antagonists and certain of these compounds are also thromboxane synthetase inhibitors or cyclooxygenase inhibitors, or anti-inflammatory agents in the manner of aspirin and indomethacin.

Mochizuki et al, "Thromboxane $A_2$ Antagonistic Action of a New Anti-Ulcer Agent, Azuletil Sodium (KT1-32)," Scand. J. Gastroenterol 1989, 24 (suppl 162), 194–197 disclose that KT1-32 (sodium 3-ethyl-7-(1-methylethyl)-1-azulenesulfonate), a competitive $TXA_2/PGH_2$ receptor antagonist "may be a promising drug for the treatment of peptic ulcers accompanied by hemorrhage (page 197)."

DESCRIPTION OF THE INVENTION

In accordance with the present invention, a method is provided for protecting against and/or treating ulcerative and inflammatory conditions of the gastrointestinal tract, including anti-inflammatory drug-induced gastrointestinal ulcers, wherein a therapeutic amount of a thromboxane $A_2$ receptor antagonist which is a 7-oxabicycloheptane or 7-oxabicycloheptene prostaglandin analog, is systemically administered, such as orally or parenterally, to a mammalian species in need of such treatment.

In addition, in accordance with the present invention, a method is provided for protecting against and/or treating pain and/or inflammation, while inhibiting formation of gastrointestinal ulcers, wherein a therapeutic amount of a combination of an anti-inflammatory drug and a thromboxane $A_2$ receptor antagonist is systemically administered, such as orally or parenterally, to a mammalian species in need of such treatment.

The term "ulcerative and inflammatory conditions of the gastrointestinal tract" as employed herein includes conditions such as gastric ulcers, duodenal ulcers, Crohn's disease, ulcerative colitis, irritable bowel syndrome, and inflammatory bowel disease.

Further, in accordance with the present invention, a new combination is provided which includes a thromboxane $A_2$ receptor antagonist and an anti-inflammatory drug which may be employed in a weight ratio to each other of within the range of from about 0.01:1 to about 100:1, and preferably from about 0.5:1 to about 2:1.

The above combination may be employed to treat pain, joint swelling, and stiffness associated with rheumatoid arthritis or to treat diseases in the manner of known anti-inflammatory agents.

As indicated, adverse effects of anti-inflammatory drugs on the gastrointestinal system seriously limit chronic use thereof. In accordance with the present invention, it has been found that thromboxane $A_2$ receptor antagonists inhibit and in some cases, prevent side effects associated with use of anti-inflammatory drugs without diminishing the efficacy thereof. Thus, thromboxane $A_2$ receptor antagonists may be used concurrently with anti-inflammatory drugs to improve the clinical safety of such anti-inflammatory drugs.

Anti-inflammatory drugs or agents which may be employed herein include, but are not limited to, aspirin, indomethacin, ibuprofen, meclofenamate, naproxen, phenylbutazone, piroxicam, and various corticosteroids including hydrocortisone, dexamethasone, and methylpredisolone.

Thromboxane $A_2$ receptor antagonists which may be employed herein include 7-oxabicycloheptane substituted diamide prostaglandin analogs of U.S. Pat. No. 4,663,336 to Nakane et al having the formula

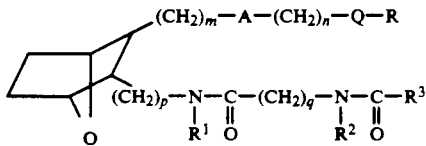

including all stereoisomers thereof, wherein m is 0 to 4; A is —CH=CH— or —CH$_2$—CH$_2$—; n is 1 to 5; Q is —CH=CH—, —CH$_2$—,

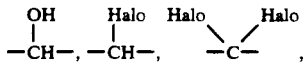

or a single bond; R is CO$_2$H, CO$_2$alkyl, CO$_2$ alkali metal, CO$_2$polyhydroxyamine salt, —CH$_2$OH,

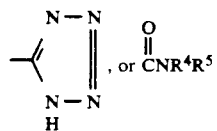

wherein R$^4$ and R$^5$ are the same or different and are H, lower alkyl, hydroxy, lower alkoxy or aryl at least one of R$^4$ and R$^5$ being other than hydroxy and lower alkoxy; p is 1 to 4; R$^1$ is H or lower alkyl, q is 1 to 12; R$^2$ is H or lower alkyl; and R$^3$ is H, lower alkyl, lower alkenyl, lower alkynyl, aryl, arylalkyl, lower alkoxy, arylalkyloxy, aryloxy, amino, alkylamino, arylalkylamino, arylamino,

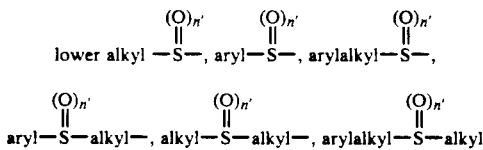

(wherein n' is 0, 1 or 2), alkylaminoalkyl, arylaminoalkyl, arylalkylaminoalkyl, alkoxyalkyl, aryloxyalkyl or arylalkoxyalkyl; and interphenylene 7-oxabicycloheptane substituted heterocyclic amide prostaglandin analogs of Misra et al U.S. patent application Ser. No. 334,070 filed Apr. 30, 1989, now abandoned, having the formula

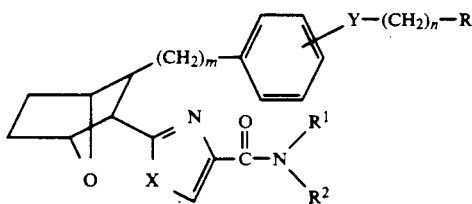

and including all stereoisomers thereof, wherein m is 1, 2 or 3; n is 0, 1, 2, 3 or 4;

Y is O or a single bond, with the proviso that when n is 0, Y is a single bond;

R is CO$_2$H, CO$_2$lower alkyl, CO$_2$alkali metal, CONHSO$_2$R$^3$ or 5-tetrazolyl, with the proviso that when R is 5-tetrazolyl, n cannot be 0;

X is O, S or NH;

R$^1$ is lower alkyl, aryl, cycloalkyl, saturated heterocycle or aromatic heterocycle, each optionally substituted with an alkyl, aryl, cycloalkyl, or cycloalkylalkyl;

R$^2$ is hydrogen, lower alkyl, aryl or aralkyl; or R$^1$ and R$^2$ together with the nitrogen to which they are linked may form a 5- to 8-membered ring; and R$^3$ is lower alkyl, aryl or aralkyl.

The interphenylene 7-oxabicycloheptyl substituted heterocyclic amide prostaglandin analogs disclosed in abandoned application Ser. No. 334,070 may have the formula

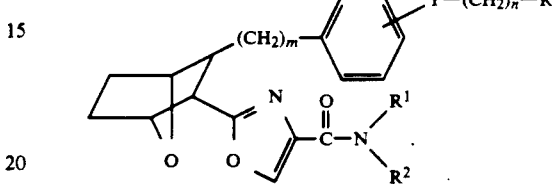

Thromboxane A$_2$ receptor antagonists which may be employed herein include the 7-oxabicycloheptane and 7-oxabicycloheptene compounds disclosed in U.S. Pat. No. 4,537,981 to Snitman et al, especially [1S-[1α,-2α(Z),3α(1E,3S*,4R*),4α]]-7-[3-(3-hydroxy-4-phenyl-1-pentenyl)-7-oxabicyclo[2.2.1]-hept-2-yl]-5-heptenoic acid (SQ 29,548); the 7-oxabicycloheptane substituted aminoprostaglandin analogs disclosed in U.S. Pat. No. 4,416,896 to Nakane et al, especially, [1S-[1α,2α(Z)-,3α4α]]-7-[3-[[2-(phenylamino)carbonyl]hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, especially, [1S-[1α,2α(Z),3α,4α]]-7-[3-[[[[(1-oxoheptyl)amino]acetyl]amino]methyl]-7-oxabicyclo[2.2.1]hept-2-yl]-5-heptenoic acid and the corresponding tetrazole, and [1S-[1α,2α(Z),3α,4α]]-7-[3-[[[[(4-cyclohexyl-1-oxobutyl)amino]acetyl]amino]-methyl]-7-oxabicyclo[2.2.1]hept-2-yl]-5-heptenoic acid; interphenylene 7-oxabicycloheptyl substituted heterocyclic amide prostaglandin analogs as disclosed in U.S. Pat. No. 5,100,889 to Misra et al, including [1S-(1α,2α,-3α,4α)]-2-[[3-[4-[[(4-cyclohexylbutyl)amino]carbonyl]-2-oxazolyl]-7-oxabicyclo[2.2.1]hept-2-yl]methyl]benzenepropanoic acid, (SQ 33,961) which is preferred, or esters or salts thereof; [1S-(1α,2α,3α,4α)]-2-[[3-[4-[[[(4-chlorophenyl)butyl]amino] carbonyl]-2-oxazolyl]-7-oxabicyclo[2.2.1]hept-2-yl]methyl]benzenepropanoic acid or esters, or salts thereof; [1S-(1α,2α,3α,4α)]-3-[[3-[4-[[(4-cyclohexylbutyl)amino]carbonyl]-2-oxazolyl]-7-oxabicyclo[2.2.1]hept-2-yl]methyl]benzeneacetic acid, or esters or salts thereof; [1S-(1α,2α,3α,4α)]-[2-[[3-[4-[[(4-cyclohexylbutyl)amino]carbonyl]-2-oxazolyl]-7-oxabicyclo[2.2.1]hept-2-yl]methyl]phenoxy]acetic acid, or esters or salts thereof; [1S-(1α,2α,3α,4α)]-2-[[3-[4-[[[(7,7-dimethyloctyl)amino]carbonyl]-2-oxazolyl]-7-oxabicyclo[2.2.1]hept-2-yl]methyl]benzenepropanoic acid, or esters or salts thereof; 7-oxabicycloheptyl substituted heterocyclic amide prostaglandin analogs as disclosed in U.S. application Ser. No. 442,818, filed Nov. 28, 1989 including [1S-[1α,2α(Z),3α,4α]]-6-[3-[4-[[(4-cyclohexylbutyl)amino]carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[[(4-cyclohexylbutyl)amino]carbonyl]-2-thiazolyl]-7-oxabicyclo[2.2.1]hept-2-yl]-4-hexenoic acid, or esters or salts thereof; [1S[1α,2α(Z),3α,4α]]-6-[3-[4-[[(4-cyclohexylbutyl)methylamino]carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[(1-pyrrolidinyl)carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[(cyclohexylamino)carbonyl]-2-oxazolyl]-7-oxabicyclo[2.2.1]hept-2-yl]-4-hexenoic acid or esters or salts thereof; [1S-[1α,2α(Z),3α,4α]]-6-[3-[4-[[(2-cyclohexylethyl)amino]carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[[[2-(4-chlorophenyl)ethyl]amino]carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[[(4-chlorophenyl)amino]carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[[[4-(4-chlorophenyl)butyl]amino]carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4a-[[(6-cyclohexylhexyl)amino]carbonyl]-2-oxazolyl]-7-oxabicyclo[2.2.1]hept-2-yl]-4-hexenoic acid, or esters, or salts thereof; [1S-[1α,2α(Z),3β,4α]]-6-[3-[4-[[(6-cyclohexylhexyl)amino]carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[(propylamino)carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[[(4-butylphenyl)amino]carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[[(2,3-dihydro-1H-indol-1-yl)carbonyl]-2-oxazolyl]-7-oxabicyclo[2.2.1]hept-2-yl]-4-hexenoic acid, or esters or salts thereof; [1S-[1α,2α(Z),3α,4α]]-6-[3-[4-[[(4-cyclohexylbutyl)amino]carbonyl]-2-oxazolyl]-7-oxabicyclo[2.2.1]hept-2-yl]-N-(phenylsulfonyl)-4-hexenamide; [1S-[1α,2α(Z),3α,4α]]-6-[3-[4-[[(4-cyclohexylbutyl)amino]carbonyl]-2-oxazolyl]-N-(methylsulfonyl)-7-oxabicyclo[2.2.1]-hept-2yl]-4-hexenamide; [1S-[1α,2α(Z),3α,4α]]-7-[3-[4-[[(4-cyclohexylbutyl)amino]carbonyl]-2-oxazolyl]-7-oxabicyclo[2.2.1]hept-2-yl]-5-heptenoic acid, or esters or salts thereof; [1S-1α,2α(Z),3α,4α]]-6-[3-[4-[[(4-cyclohexylbutyl)amino]carbonyl]-1H-imidazol-2-yl]-7-oxabicyclo[2.2.1]hept-2-yl]-4-hexenoic acid or esters or salts thereof; [1S-[1α,2α,3α,4α]-6-[3-[4-[[(7,7-dimethyloctyl)amino]carbonyl]-2-oxazolyl]-7-oxabicyclo[2.2.1]hept-2-yl]-4-hexenoic acid, or esters or salts thereof; [1S-[1α,2α(E),3α,4α]]-6-[3-[4-[[(4-cyclohexylbutyl)amino]carbonyl]-2-oxazolyl]-7-oxabicyclo[2.2.1]hept-2-yl]-4-hexenoic acid; [1S-(1α,2α,3α,4α)]-3-[4-[[(4-(cyclohexylbutyl)amino]carbonyl]-2-oxazolyl]-7-oxabicyclo[2.2.1]heptane-2-hexanoic acid or esters or salts thereof, with a preferred compound being [1S-[1α,2α(Z),3α4α]]-6-[3-[4-[[(4-cyclohexylbutyl)amino]carbonyl]-2-oxazolyl]-7-oxabicyclo[2.2.1]hept-2-yl]-4-hexenoic acid, or esters or salts thereof; 7-oxabicycloheptane imidazole prostaglandin analogs as disclosed in U.S. application Ser. No. 364,408, filed Jun. 12, 1989, including [1S-[1α,2α(Z),3α,4α]]-6-[3-[[4-(4-cyclohexyl-1-hydroxybutyl)-1H-imidazol-1-yl]methyl]-7-oxabicyclo[2.2.1]hept-2-yl]-4-hexenoic acid or its methyl ester; [1S-[1α,2α(Z),3α,4α]]-6-[3-[[4-(3-cyclohexylpropyl)-1H-imidazol-1-yl]methyl]-7-oxabicyclo[2.2.1]hept-2-yl]-4-hexenoic acid or its methyl ester; [1S-[1α,2α(Z),3α,4α]]-6-[3-[[4-(4-cyclohexyl-1-oxobutyl)-1H-imidazol-1-yl]methyl]-7-oxabicyclo[2.2.1]hept-2-yl]-4-hexenoic acid or its methyl ester; [1S-[1α,2α(Z),3α,4α]]-6-[3-(1H-imidazol-1-ylmethyl)-7-oxabicyclo[2.2.1]hept-2-yl]-4-hexenoic acid or its methyl ester; or [1S-[1α,2α(Z),3α,4α]]-6-[3-[[4-[[(4-cyclohexylbutyl)amino]carbonyl]-1H-imidazol-1-yl]methyl-7-oxabicyclo[2.2.1]hept-2-yl]-4-hexenoic acid, or its methyl ester; the phenoxyalkyl carboxylic acids disclosed in U.S. Pat. No. 4,258,058 to Witte et al, especially 4-[2-(benzenesulfamido)ethyl]phenoxyacetic acid (BM 13,177 - Boehringer Mannheim), the sulphonamidophenyl carboxylic acids disclosed in U.S. Pat. No. 4,443,477 to Witte et al, especially 4-[2-(4-chlorobenzenesulfonamido)ethyl]phenylacetic acid (BM 13,505, Boehringer Mannheim), the arylthioalkylphenyl carboxylic acids disclosed in U.S. Pat. No. 4,752,616, especially 4-(3-((4-chlorophenyl)sulfonyl)propyl)benzeneacetic acid.

Other examples of thromboxane $A_2$ receptor antagonists suitable for use herein include, but are not limited to (E)-5-[[[(pyridinyl)[3-trifluoromethyl)phenyl]methylene]amino]oxy]pentanoic acid also referred to as R68,070 - Janssen Research Laboratories, 3-[1-(4-chlorophenylmethyl)-5-fluoro-3-methylindol-2-yl]-2,2-dimethylpropanoic acid [(L-655240 Merck-Frosst) Eur. J. Pharmacol. 135(2):193, Mar. 17, 87],5(Z)-7-([2,4,5-cis]-4-(2-hydroxyphenyl)-2-trifluoromethyl-1,3-dioxan-5-yl)heptenoic acid (ICI 185282, Brit. J. Pharmacol. 90 (Proc. Suppl):228 P-Abs., March 87), 5(Z)-7-[2,2-dimethyl-4-phenyl-1,3-dioxan-cis-5-yl]heptenoic acid (ICI 159995, Brit. J. Pharmacol. 86 (Proc. Suppl):808 P-Abs., December 85), N,N'-bis[7-(3-chlorobenzeneaminosulfonyl)-1,2,3,4-tetrahydro-isoquinolyl]-disulfonylimide (SKF 88046, Pharmacologist 25(3):116 Abs., 117 Abs. August 83), [1α(Z)-2β,5α]-(+)-7-[5-[[(1,1'-biphenyl)-4-yl]methoxy]-2-(4-morpholinyl)-3-oxocyclopentyl]-4-heptenoic acid (AH 23848 - Glaxo, Circulation 72(6):1208, December 85, levallorphan allyl bromide (CM 32,191 Sanofi, Life Sci. 31 (20–21):2261, Nov. 15, 82), (Z,2-endo-3-oxo)-7-(3-acetyl-2-bicyclo[2.2.1]heptyl-5-hepta-3'Z-enoic acid, 4-phenylthiosemicarbazone (EP092 - Univ. Edinburgh, Brit. J. Pharmacol. 84(3):595, March 85); GR32,191 - [1R-[1α(Z),2β,3β,5α]]-(+)-7-[5-([1,1'-biphenyl]-4-ylmethoxy)-3-hydroxy-2-(1-piperidinyl)cyclopentyl]-4-heptenoic acid; ICI 192,605 - 4(Z)-6-[(2,4,5-cis)2-(2-chlorophenyl)-4-(2-hydroxyphenyl)1,3-dioxan-5-yl]hexenoic acid; BAY u 3405 - 3-[[(4-fluorophenyl)sulfonyl]amino]-1,2,3,4-tetrahydro-9H-carbazole-9-propanoic acid; or ONO 3708 - 7-[2α,4α-(di-methylmethano)-6β-(2-cyclopentyl-2β-hydroxyacetamido)-1α-cyclohexyl]-5(Z)-heptenoic acid; (±)(5Z)-7-[3-endo-[(phenylsulfonyl)amino]bicyclo[2.2.1]hept-2-exo-yl]heptenoic acid (S-145, Shionogi); (—)6,8-difluoro-9-p-methylsulfonylbenzyl-1,2,3,4-tetrahydrocarbazol-1-yl-acetic acid (L670596, Merck) and (3-[1-(4-chlorobenzyl)-5-fluoro-3-methyl-indol-2-yl]2,2-dimethylpropanoic acid (L655240, Merck).

The disclosure of the above-mentioned U.S. patents and U.S. patent applications are incorporated herein by reference.

In carrying out the method of the present invention, the thromboxane $A_2$ antagonist alone or in combination with the anti-inflammatory compound may be administered to mammalian species, such as monkeys, dogs, cats, rats, humans, etc., systemically, such as orally or parenterally, as well as intraperitoneally, topically, or by inhalation.

The thromboxane $A_2$ antagonist alone or in combination with the anti-inflammatory agent may be incorporated in a conventional dosage form, such as a tablet, capsule, elixir, cream, suppository, aerosol spray or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The thromboxane $A_2$ antagonist may be employed in a separate dosage form from the anti-inflammatory agent such as two separate injections and/or tablets or the two may be employed in a single dosage form, such as a single injection and/or tablet.

With regard to such systemic formulations, wherein the thromboxane $A_2$ antagonist is to be employed alone, single or divided doses of from about 0.1 to about 2500 mg, preferably from about 2 to about 2000 mg, one to eight times daily, may be administered in systemic dosage forms as described above.

With regard to combinations of the thromboxane $A_2$ antagonist with anti-inflammatory agent, single or divided doses of from 0.1 to about 2500 mg of thromboxane $A_2$ antagonist, preferably 2 to 2000 mg thromboxane $A_2$ antagonist, and from about 2 to about 2000 mg anti-inflammatory agent and preferably from about 5 to about 1500 mg anti-inflammatory agent, depending upon the type of anti-inflammatory agent employed, may be administered one to eight times daily.

It will be appreciated that all of the anti-inflammatory drugs disclosed herein are known for treating inflammation and/or pain and may be employed in dosage forms and amounts as disclosed in the Physicians' Desk Reference.

REFERENCES TO ACCOMPANYING FIGURES

Figure 2:
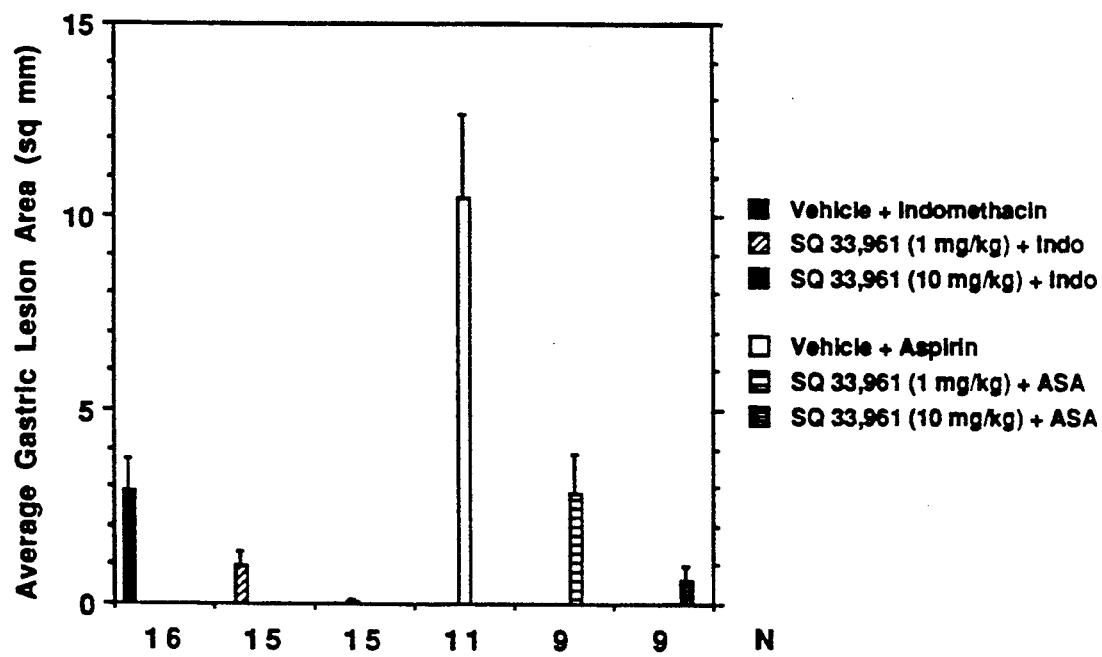

FIG. 1 is a graph of the effect of SQ 33,961 on taurocholic acid induced gastric ulcers in rats; and FIG. 2 is a graph of the effect of SQ 33,961 on aspirin- and indomethacin-induced gastric ulcers.

The following Examples represent preferred embodiments of the present invention.

EXAMPLE 1

A thromboxane $A_2$ antagonist formulation suitable for oral administration for use in preventing or treating ulcers is set out below.

1000 tablets each containing 400 mg of thromboxane $A_2$ receptor antagonist were produced from the following ingredients.

| | |
|---|---|
| [1S-[1α,2α(Z),3α,4α]]-7-[3-[[[[(1-Oxoheptyl)amino]acetyl]amino]methyl]-7-oxabicyclo[2.2.1]hept-2-yl]-5-heptenoic acid (SQ 30,741) | 400 g |
| Corn starch | 50 g |
| Gelatin | 7.5 g |
| Avicel (microcrystalline cellulose) | 25 g |
| Magnesium stearate | 2.5 g |

The thromboxane $A_2$ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

EXAMPLES 2 TO 7

Tablets for use in preventing or treating ulcers are prepared as described in Example 1 except that the thromboxane $A_2$ receptor antagonist employed is [1S-[1α,2α(Z),3α,4α]]-7-[3-[[[[(4-cyclohexyl-1-oxobutyl)amino]acetyl]amino]methyl]-7-oxabicyclo-[2.2.1]hept-2-yl]-5-heptenoic acid; GR 32,191; ICI 192,605; R-68,070; BAY u 3405; or ONO 3708.

EXAMPLE 8

An injectable solution of thromboxane $A_2$ receptor antagonist for intravenous use in preventing or treating ulcers is produced as follows.

| | |
|---|---|
| SQ 30,741 | 2500 mg |
| Methyl paraben | 5 mg |
| Propyl paraben | 1 mg |
| Sodium chloride | 25 g |
| Water for injection qs. | 5 l. |

The thromboxane $A_2$ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 9

An injectable for use in treating and/or preventing ulcers is prepared as described in Example 1 except that the thromboxane $A_2$ receptor antagonist employed is the phenoxyalkyl carboxylic acid 4-[2-(benzenesulfamido)ethyl]phenoxyacetic acid, disclosed in U.S. Pat. No. 4,258,058.

EXAMPLE 10

An injectable solution of thromboxane $A_2$ receptor antagonist for intravenous use containing [1S-[1α,2α(Z),3α,4α]]-7-[3-[[[[(1-oxoheptyl)amino]acetyl]amino]methyl]-7-oxabicyclo[2.2.1]hept-2-yl]-5-heptenoic acid (SQ 30,741) as the thromboxane $A_2$ receptor antagonist is prepared as described in Example 8.

EXAMPLE 11

An injectable solution of thromboxane $A_2$ receptor antagonist for intravenous use in preventing or treating ulcers is prepared as follows.

| | |
|---|---|
| [1S-(1α,2α,3α,4α)]-2-[[3-[4-[[(4-cyclohexylbutyl)amino]carbonyl]-2-oxazolyl]-7-oxabicyclo[2.2.1]hept-2-yl]methyl]benzenepropanoic acid SQ 33,961) | 2500 mg |
| Methyl paraben | 5 mg |
| Propyl paraben | 1 mg |
| Sodium chloride | 25 g |
| Water for injection qs. | 5 l. |

The thromboxane $A_2$ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 mL of solution.

EXAMPLE 12

Tablets for use in treating or preventing ulcers are prepared as described in Example 1 except that the thromboxane A$_2$ receptor antagonist employed is [1S-[1α,2α(Z),3α,4α]]-6-[3-[4-[[(4-cyclohexylbutyl)amino]-carbonyl]-2-oxazolyl]-7-oxabicyclo-[2.2.1]hept-2-yl]-4-hexenoic acid.

EXAMPLE 13

An injectable solution of thromboxane A$_2$ receptor antagonist for intravenous use containing [1S-[1α,2α(Z),3α(IE,3S*,4R*),4α]]-7-[3-(3-hydroxy-4-phenyl-1-pentenyl)-7-oxabicyclo[2.2.1]hept-2-yl]-5-heptenoic acid (SQ 29,548) as the thromboxane A$_2$ receptor antagonist is prepared as described in Example 8.

EXAMPLE 14

A thromboxane A$_2$ antagonist formulation suitable for oral administration is set out below.

1000 tablets each containing 40 mg of thromboxane A$_2$ receptor antagonist are produced from the following ingredients.

| | |
|---|---|
| SQ 33,961 | 40 g |
| Corn starch | 50 g |
| Gelatin | 7.5 g |
| Avicel (microcrystalline cellulose) | 25 g |
| Magnesium stearate | 2.5 g |

The thromboxane A$_2$ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 40 mg of active ingredient.

EXAMPLES 15 TO 23

The formulation as described in Examples 1 to 7 and 14 was prepared except that 650 mg of aspirin was included in each tablet or dose equivalent.

EXAMPLES 24 TO 32

The formulation as described in Examples 1 to 7 and 14 was prepared except that 50 mg of indomethacin was included in each tablet or dose quivalent.

EXAMPLES 33 AND 41

The formulation as described in Examples 1 to 7 and 14 was prepared except that 50 mg of meclofenamate was included in each tablet or dose equivalent.

EXAMPLE 42 TO 50

The formulations as described in Examples 1 to 7 and 14 were prepared except that 50 mg of ibuprofen was included in each tablet or dose equivalent.

EXAMPLE 51 TO 59

The formulation as described in Examples 1 to 7 and 14 were prepared except that 250 mg of naproxen was included in each tablet or dose equivalent.

EXAMPLE 60

The following experiment was conducted to determine the cytoprotective potential of the thromboxane receptor antagonist SQ 33,961 on taurocholic acid-induced ulcers in rats.

Fasted rats were treated with either vehicle (9.5% ethanol in 0.02% Na$_2$CO$_3$, pH 9; 5 mL/kg, i.p.) or SQ 33,961 (0.01 to 10 mg/kg, i.p.) 60 minutes before administration of either vehicle (0.2N HCl, pH 2; 1.0 mL, p.o.) or taurocholic acid (100 mM, pH 2; 1.0 mL, p.o.). One hour later, rats were sacrificed and gastric lesion number and areas measured. There were no gastric erosions in the groups of rats challenged with the taurocholic acid vehicle. In rats challenged with taurocholic acid gastric lesions developed and SQ 33,961 produced a dose-related reduction of gastric lesion area, with an ID$_{50}$ of 12 μg/kg, i.p. This finding, summarized in FIG. 1, supports the pivotal involvement of thromboxane receptor activation in this model of bile acid induced gastric erosion.

EXAMPLE 61

The following experiment was carried out to evaluate thromboxane receptor involvement in other models of gastro-intestinal ulcer.

In two studies, SQ 33,961 (1 and 10 mg/kg, i.p.) was evaluated in models of gastric ulcer induced by indomethacin (20 mg/kg, s.c.) and aspirin (200 mg/kg, p.o.). In each of these experiments, a dose of SQ 33,961 or vehicle (9.5% ethanol in 0.02% Na$_2$CO$_3$, pH 9; 5 mL/kg) was administered by intraperitoneal injection 60 minutes before administration of aspirin, aspirin vehicle (1% methyl cellulose; 5 mL/kg, p.o.), indomethacin, or indomethacin vehicle (3.2% Na$_2$CO$_3$, pH 8; 5 mL/kg, s.c.) in fasted male Sprague-Dawley rats (174–352 g). Three hours later, the rats were sacrificed by CO$_2$ asphyxiation, the stomachs excised and opened, the lumen rinsed with saline, and the number and areas of gastric lesions measured.

Under these experimental conditions, aspirin caused more severe gastric lesions than indomethacin. Average total lesion areas were 10.5±2.1 mm$^2$ (N=11) and 2.9±0.8 mm$^2$ (N=16) for aspirin and indomethacin, respectively. As shown in the following Table 1 and in FIG. 2, the 1 and 10 mg/kg doses of Sq 33,961 produced respectively about 70% and 95% inhibition of gastric erosions in both aspirin and indomethacin treated rats. None of the rats given the aspirin vehicle or indomethacin vehicle developed gastric lesions.

TABLE 1

| Ulcer Score (# of rats) | % Ulcer Inhibition |
|---|---|
| Aspirin (200 mg/kg, p.o.) + Vehicle (CONTROL) 10.5 ± 2.01 (11) | — |
| Aspirin (200 mg/kg, p.o.) + SQ 33,961 (1 mg/kg, i.p.) 2.86 ± 1.02 (9) | 73% |
| Aspirin (200 mg/kg, p.o.) + SQ 33,691 (10 mg/kg, i.p.) 0.62 ± 0.34 (9) | 94% |
| Indomethacin (20 mg/kg, s.c.) + Vehicle (CONTROL) 2.90 ± 0.81 (16) | — |
| Indomethacin (20 mg/kg, s.c.) + SQ 33,961 (1 mg/kg, i.p.) 0.94 ± 0.41 (15) | 68% |
| Indomethacin (20 mg/kg, s.c.) + SQ 33,961 (10 mg/kg, i.p.) 0.08 ± 0.07 (15) | 97% |

EXAMPLE 62

The ability of SQ 33,961 to inhibit the anti-inflammatory activities of non-steroidal anti-inflammatory drugs (NSAIDs) was tested in the standard carrageenan paw edema model in rats.

One hour before intraplantar injection of carrageenan, SQ 33,961 (10 mg/kg) or vehicle was injected i.p., and 30 minutes later i.p. indomethacin (10 mg/kg) or vehicle was administered. Paw volumes were measured before and hourly after carageenan injection in the 4 groups (N=7-8 each). Carrageenan caused a significant increase in paw volume that plateaued from 3-5 hours after injection.

TABLE 2

Paw Volume in mL (# of rats) 3 hours after Carrageenan injection
Vehicle + Vehicle (Control)
2.7 ± 0.05 (8)
Vehicle + Indomethacin
2.2 ± 0.08 (8) p = 0.001 vs Vehicle + Vehicle
SQ 33,961 + Vehicle
2.6 ± 0.11 (7) NS* vs Vehicle + Vehicle
SQ 33,961 + Indomethacin
2.3 ± 0.12 (7) p < 0.02 vs Vehicle + Vehicle
NS vs Vehicle + Indomethacin

*NS = not significant

The results obtained indicate that SQ 33,961 had no significant effect on the development of paw edema. Indomethacin significantly inhibited edema formation, and this antiphlogistic activity was not inhibited by SQ 33,961. Thus, SQ 33,961 inhibits NSAID-induced gastric ulceration without influencing anti-inflammatory activity.

EXAMPLE 63

In the aspirin-induced ulcer model in which SQ 33,961 produced dose related reductions in gastric erosions, the thromboxane synthetase inhibitor dazoxiben did not diminish aspirin-induced gastric erosions, but the thromboxane antagonist BM 13,505 significantly diminished aspirin-induced gastric erosions. Table 3 summarizes results obtained.

TABLE 3

| | Effects of Thromboxane antagonists on Aspirin*-Induced Ulcer | | |
|---|---|---|---|
| Test Agent | Dose (mg/kg, i.p.) | N | Average Gastric Lesion Area (mm²) |
| Vehicle | — | 16 | 9.98 ± 1.73 |
| SQ 33,961 | 0.1 | 6 | 6.21 ± 1.66 |
| SQ 33,961 | 1.0 | 9 | 2.86 ± 1.02 |
| SQ 33,961 | 10.0 | 9 | 0.62 ± 0.34 |
| Dazoxiben (TXA₂ synthetase inhibitor) | 50.0 | 6 | 25.40 ± 8.50 |
| Vehicle | — | 11 | 11.18 ± 2.35 |
| BM 13,505 (TXA₂ receptor antagonist) | 20.00 | 9 | 4.68 ± 1.63 |

*Aspirin Dose = 200 mg/kg, p.o. 1 hour after dosing with Test Agent. Rats were sacrificed and ulcers measured 3 hours after aspirin administration.

What is claimed is:

1. A method for preventing or treating ulcerative conditions of the gastrointestinal tract, in a mammalian species, which comprises administering to a mammalian species in need of such treatment an effective amount of a thromboxane $A_2$ receptor antagonist, which is a 7-oxabicycloheptane substituted diamide prostaglandin analog, or an interphenylene 7-oxabicycloheptyl substituted heterocyclic amide prostaglandin analog, said 7-oxabicycloheptane substituted diamide prostaglandin having the formula

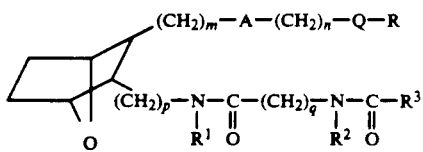

including all stereoisomers thereof, wherein m is 0 to 4; A is —CH=CH— or —CH₂—CH₂—; n is 1 to 5; Q is —CH=CH—, —CH₂—, $$-\underset{\underset{\text{OH}}{|}}{\text{CH}}-, \ -\underset{\underset{\text{Halo}}{|}}{\text{CH}}-, \ -\underset{\underset{\text{Halo}}{\diagup}}{\overset{\overset{\text{Halo}}{\diagdown}}{\text{C}}}- \ ,$$

or a single bond; R is $CO_2H$, $CO_2$alkyl, $CO_2$ alkali metal, $CO_2$polyhydroxyamine salt, —CH₂OH, $$-\!\!\!\!\begin{array}{c} \text{N} - \text{N} \\ \diagup \quad \diagdown \\ \diagdown \quad \diagup \\ \text{N} - \text{N} \\ | \\ \text{H} \end{array}\!\!\!\!, \ \text{or} \ \overset{\text{O}}{\underset{\|}{\text{C}}}\text{NR}^4\text{R}^5$$

wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; q is 1 to 12; $R^2$ is H or lower alkyl; and $R^3$ is H, lower alkyl, lower alkenyl, lower alkynyl, aryl, arylalkyl, lower alkoxy, arylalkyloxy, aryloxy, amino, alkylamino, arylalkylamino, arylamino, $$\text{lower alkyl} -\overset{(O)_{n'}}{\underset{\|}{S}}-, \text{ aryl}-\overset{(O)_{n'}}{\underset{\|}{S}}-, \text{ arylalkyl}-\overset{(O)_{n'}}{\underset{\|}{S}}-,$$

$$\text{aryl}-\overset{(O)_{n'}}{\underset{\|}{S}}-\text{alkyl}-, \text{ alkyl}-\overset{(O)_{n'}}{\underset{\|}{S}}-\text{alkyl}-, \text{ arylalkyl}-\overset{(O)_{n'}}{\underset{\|}{S}}-\text{alkyl}$$

(wherein n' is 0, 1 or 2), alkylaminoalkyl, arylaminoalkyl, arylalkylaminoalkyl, alkoxyalkyl, aryloxyalkyl or arylalkoxyalkyl, and said interphenylene 7-oxabicycloheptane substituted heterocyclic amide prostaglandin analog having the formula and including all stereoisomers thereof, wherein
m is 1, 2 or 3; n is 0, 1, 2, 3 or 4;
Y is O or a single bond, with the proviso that when n is 0, Y is a single bond;
R is $CO_2H$, $CO_2$lower alkyl, $CO_2$alkali metal, $CONHSO_2R^3$ or 5-tetrazolyl, with the proviso that when R is 5-tetrazolyl, n cannot be 0;
X is O, S or NH;

R[1] is lower alkyl, aryl, cycloalkyl, saturated heterocycle or aromatic heterocycle, each optionally substituted with an alkyl, aryl, cycloalkyl, or cycloalkylalkyl;

R[2] is hydrogen, lower alkyl, aryl, or aralkyl; or R[1] and R[2] together with the nitrogen to which they are linked may form a 5- to 8-membered ring; and R[3] is lower alkyl, aryl or aralkyl.

2. The method as defined in claim 1 wherein the interphenylene 7-oxabicycloheptyl substituted heterocyclic amide prostaglandin has the formula

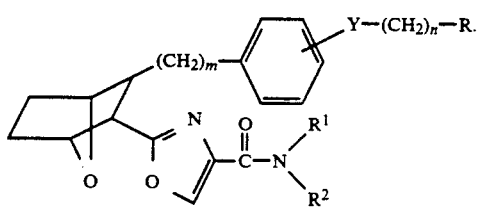

3. The method as defined in claim 1 wherein the thromboxane A$_2$ receptor antagonist is [1S-[1α,2α(Z)-,3α,4α]]-7-[3-[[[[(1-oxoheptyl)amino]acetyl]amino]methyl]-7-oxabicyclo-[2.2.1]hept-2-yl]-5-heptenoic acid or the corresponding tetrazole; [1S-[1α,2α(Z),3α,4α]]-7-[3-[[[[(4-cyclohexyl-1-oxobutyl)amino]acetyl]amino]methyl]-7-oxabicyclo[2.2.1]hept-2-yl]-5-heptenoic acid; [1S-(1α,2α,3α,4α)]-2-[[3-[4-[[(4-cyclohexylbutyl)amino]carbonyl]-2-oxazolyl]-7-oxabicyclo-[2.2.1]hept-2-yl]methyl]benzenepropanoic acid (SQ33,961) or esters or salts thereof; [1S-(1α,2α,3α,4α)]-2-[[3-[4-[[[(4-chlorophenyl)butyl]amino]carbonyl]-2-oxazolyl]-7-oxabicyclo-[2.2.1]hept-2-yl]methyl]benzenepropanoic acid or esters, or salts thereof; [1S-(1α,2α,3α,4α)-3-[[3-[4-[[(4-cyclohexylbutyl)amino]carbonyl]-2-oxazolyl]-7-oxabicyclo[2.2.1]hept-2-yl]methyl]benzeneacetic acid, or esters or salts thereof; [1S-(1α,2α,3α,4α)]-2-[[3-[4-[[[(4-cyclohexylbutyl)amino]carbonyl]-2-oxazolyl]-7-oxabicyclo[2.2.1]hept-2-yl]methyl]phenoxy]acetic acid, or esters or salts thereof; or [1S-(1α,2α,3α,4α)]-2-[[3-[4-[[[(4-dimethyloctyl)amino]carbonyl]-2-oxazolyl]-7-oxabicyclo[2.2.1]hept-2-yl]methyl]benzenepropanoic acid, or esters or salts thereof.

4. The method as defined in claim 1 wherein the ulcers are anti-inflammatory drug-induced.

5. A method for preventing or treating an inflammatory condition without causing gastrointestinal ulcers, in a mammalian species, which comprises administering to a mammalian species in need of such treatment an effective amount of a thromboxane A$_2$ receptor antagonist in combination with an anti-inflammatory agent, the thromboxane A$_2$ receptor antagonist being a a 7-oxabicycloheptane substituted diamide prostaglandin analog, or an interphenylene 7-oxabicycloheptyl substituted heterocyclic amide prostaglandin analog, the thromboxane A$_2$ receptor antagonist being employed in a weight ratio to the anti-inflammatory agent of within the range of from about 0.01:1 to about 100:1, said 7-oxabicycloheptane substituted diamide prostaglandin having the formula

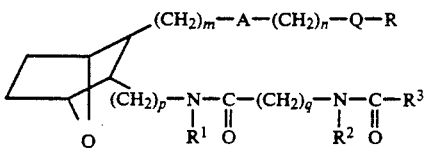

including all stereoisomers thereof, wherein m is 0 to 4; A is —CH=CH— or —CH$_2$—CH$_2$—; n is 1 to 5; O is —CH=CH—, —CH$_2$—,

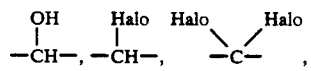

or a single bond; R is CO$_2$H, CO$_2$alkyl, CO$_2$ alkali metal, CO$_2$polyhydroxyamine salt, —CH$_2$OH,

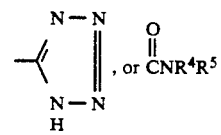

wherein R[4] and R[5] are the same or different and are H, lower alkyl, hydroxy, lower alkoxy or aryl at least one of R[4] and R[5] being other than hydroxy and lower alkoxy; p is 1 to 4; R[1] is H or lower alkyl; q is 1 to 12; R[2] is H or lower alkyl; and R[3] is H, lower alkyl, lower alkenyl, lower alkynyl, aryl, arylalkyl, lower alkoxy, arylalkyloxy, aryloxy, amino, alkylamino, arylalkylamino, arylamino,

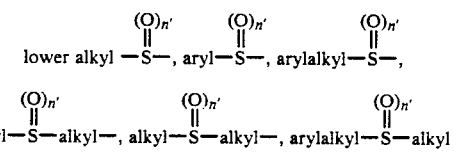

(wherein n' is 0, 1 or 2), alkylaminoalkyl, arylaminoalkyl, arylalkylaminoalkyl, alkoxyalkyl, aryloxyalkyl or arylalkoxyalkyl, and said interphenylene 7-oxabicycloheptane substituted heterocyclic amide prostaglandin analog having the formula

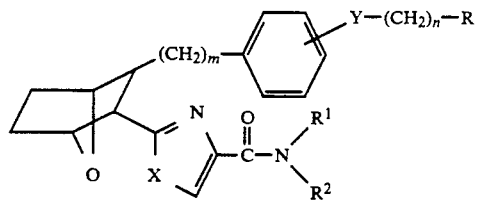

and including all stereoisomers thereof, wherein
m is 1, 2 or 3; n is 0, 1, 2, 3 or 4;
Y is O or a single bond, with the proviso that when n is 0, Y is a single bond;
R is CO$_2$H, CO$_2$lower alkyl, CO$_2$alkali metal CONHSO$_2$R[3] or 5-tetrazolyl, with the proviso that when R is 5-tetrazolyl, n cannot be 0;
X is O, S or NH;
R[1] is lower alkyl, aryl, cycloalkyl, saturated heterocycle or aromatic heterocycle, each optionally substituted with an alkyl, aryl, cycloalkyl, or cycloalkylalkyl;

R[2] is hydrogen, lower alkyl, aryl, or aralkyl; or R[1] and R[2] together with the nitrogen to which they are linked may form a 5- to 8-membered ring; and R[3] is lower alkyl, aryl or aralkyl.

6. The method as defined in claim 5 wherein the interphenylene 7-oxabicycloheptyl substituted heterocyclic amide prostaglandin has the formula

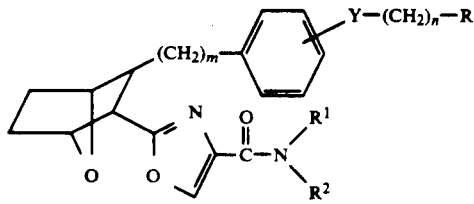

7. The method as defined in claim 6 wherein the thromboxane $A_2$ receptor antagonist is [1S-[1α,2α(Z)-,3α,4α]-7-[3-[[[[(1-oxoheptyl)amino]acetyl]amino]methyl]-7-oxabicyclo-[2.2.1]hept-2-yl]-5-heptenoic acid or the corresponding tetrazole; [1S-[1α,2α(Z),3α,4α)]]-7-[3-[[[](4-cyclohexyl-1-oxobutyl)amino]acetyl]amino]-methyl]-7-oxabicyclo[2.2.1]hept-2-yl]-5-heptenoic acid; [1S-(1α,2α,3α,4α)-2-[[3-[4-[[(4-cyclohexylbutyl)amino]-carbonyl]-2-oxazolyl]-7-oxabicyclo-[2.2.1]hept-2-yl]methyl]benzenepropanoic acid (SQ33,961) or esters or salts thereof; [1S-(1α,2α,3α,4α)]-2-[[3-[4-[[[[(4-chlorophenyl)butyl]amino]carbonyl]-2-oxazolyl]-7-oxabicyclo-[2.2.1]hept-2-yl]methyl]benzenepropanoic acid or esters, or salts thereof; [1S-(1α,2α,3α,4α)]-3-[[3-[4-[[(4-cyclohexylbutyl)-amino] carbonyl]-2-oxazolyl]-7-oxabicyclo[2.2.1]hept-2-yl]methyl]benzeneacetic acid, or esters or salts thereof; [1S-(1α,2α,3α4α)]-2-[[3-[4-[[(4-cyclohexylbutyl)amino]carbonyl]-2-oxazolyl]-7-oxabicyclo[2.2.1]hept-2-yl]methyl]phenoxy]acetic acid, or esters or salts thereof; or [1S-(1α,2α,3α,4α)]-2-[[3-[4-[[[(4-dimethyloctyl)amino]carbonyl]-2-oxazolyl]-7-oxabicyclo[2.2.1]hept-2-yl]methyl]benzenepropanoic acid, or esters or salts thereof.

8. The method as defined in claim 5 wherein the anti-inflammatory agent is aspirin, indomethacin, naproxen, ibuprofen, meclofenamate, phenylbutazone, piroxicam, or a corticosteroid.

9. The method as defined in claim 5 wherein the thromboxane receptor antagonist is SQ 33,961 and the anti-inflammatory compound is aspirin or indomethacin.

10. The method as defined in claim 5 wherein the thromboxane receptor antagonist is employed in a weight ratio to the anti-inflammatory agent of within the range of from about 0.01:1 to about 100:1.

* * * * *